(12) United States Patent
Schaneville (10) Patent No.: US 10,265,362 B2
(45) Date of Patent: Apr. 23, 2019

(54) **INGESTIBLE FILMS HAVING SUBSTANCES FROM HEMP OR *CANNABIS***

(71) Applicant: Scott Schaneville, Saint Petersburg, FL (US)

(72) Inventor: Scott Schaneville, Saint Petersburg, FL (US)

( * ) Notice: Subject to any disclaimer, the term of this patent is extended or adjusted under 35 U.S.C. 154(b) by 123 days.

(21) Appl. No.: 15/485,655

(22) Filed: Apr. 12, 2017

(65) Prior Publication Data

US 2017/0290870 A1     Oct. 12, 2017

Related U.S. Application Data

(60) Provisional application No. 62/321,480, filed on Apr. 12, 2016, provisional application No. 62/338,762, filed on May 19, 2016.

(51) Int. Cl.
| | |
|---|---|
| *A61K 36/00* | (2006.01) |
| *A61K 36/185* | (2006.01) |
| *A61K 31/352* | (2006.01) |
| *A61K 47/36* | (2006.01) |
| *A61K 47/10* | (2017.01) |
| *A61K 47/26* | (2006.01) |
| *A61K 9/00* | (2006.01) |
| *A61K 9/06* | (2006.01) |

(52) U.S. Cl.
CPC ............ *A61K 36/185* (2013.01); *A61K 9/006* (2013.01); *A61K 9/06* (2013.01); *A61K 31/352* (2013.01); *A61K 47/10* (2013.01); *A61K 47/26* (2013.01); *A61K 47/36* (2013.01)

(58) Field of Classification Search
CPC ...................................... A61K 36/00
USPC ...................................... 424/725
See application file for complete search history.

(56) References Cited

U.S. PATENT DOCUMENTS

| | | |
|---|---|---|
| 2004/0192760 A1 | 9/2004 | Whittle et al. |
| 2006/0257463 A1 | 11/2006 | Elsohly et al. |
| 2011/0028431 A1 | 2/2011 | Zerbe et al. |
| 2013/0089600 A1 | 4/2013 | Winnicki |
| 2016/0051510 A1 | 2/2016 | Allen et al. |

FOREIGN PATENT DOCUMENTS

CN          104288061 A    *    1/2015

OTHER PUBLICATIONS

PCT Written Opinion and International Search Report issued in PCT Application PCT/US2017/027144, dated Jul. 11, 2017.

* cited by examiner

*Primary Examiner* — Michael V Meller
(74) *Attorney, Agent, or Firm* — Benesch, Friedlander, Coplan & Aronoff LLP (57) ABSTRACT

Films that are mucosally dissolvable, and containing a matrix and one or more active agents from hemp or *cannabis* within the matrix, are provided. The disclosure also provides methods for preparing such a film for pharmaceutical and nutraceutical applications.

18 Claims, 6 Drawing Sheets

INGESTIBLE FILMS HAVING SUBSTANCES FROM HEMP OR CANNABIS

RELATED U.S. APPLICATION DATA

This application claims the benefit of priority to U.S. Provisional Patent Application Ser. No. 62/321,480 filed on Apr. 12, 2016 and U.S. Provisional Application Patent Application Ser. No. 62/338,762 filed on May 19, 2016, which applications are incorporated herein by reference in their entirety.

FIELD OF INVENTION

The present disclosure relates to mucosally dissolvable films containing one or more active substances, such as those obtained from hemp and/or *cannabis*, and methods of making such films for pharmaceutical or nutraceutical applications.

BACKGROUND

The *Cannabis* plant has a long history of medicinal use. The beneficial compounds in *cannabis* are used by patients to alleviate the side effects and symptoms of countless medical conditions, including pain, cancer, HIV, AIDS, multiple sclerosis, glaucoma, and more.

The *cannabis* compounds are generally administered by inhalation of smoke or vapors, ingestion of edible capsules or liquid extracts such as tinctures or oils, use of topical solutions and ingestible films or wafers. But each mode of delivery has its own disadvantages. For example, the current delivery systems of smoking, and vaporizing are unhealthy, inconvenient and lack proper dosage control. Oral administration of *cannabis*, like any medication is not always "fast-acting", a property clearly desirable in the treatment of acute breakthrough pain, for example. Besides, some pediatric and/or geriatric patients have difficulty taking an oral medication due to inability to swallow, nausea or other gastrointestinal problems. While liquid, syrups or suspensions are an alternative to solid dosage forms, such formulations often deteriorate rapidly upon exposure to heat or other atmospheric conditions and consequently have a relatively short shelf life. The films or wafers containing *cannabis* extracts are often very sticky, have a bitter after-taste and hence can contribute to patient non-compliance. In addition, conventional thin films or wafers often do not include a high load of the active ingredient.

SUMMARY

In various embodiments, the thin mucosally dissolvable film described in this disclosure contains high loading dose of purified active ingredient from *cannabis*, is easily penetrable through mucosal tissue, has improved taste profile, and is non-sticky.

The thin, mucosally dissolvable film may contain a matrix and an active agent dispersed uniformly in the matrix. The active agent being an extracted substance from *cannabis* or hemp, may include cannabinoids (CBD) or tetrahydrocannabinol (THC) in concentrations greater than about 90% and up to about 100%. When the active agent is CBD, then it may be present in a concentration of at least 90% and up to about 100%, with little or no trace of THC. When the active agent is THC, then it may be present in a concentration of at least 90% and up to about 100%, with little or no trace of CBD. The active agent may be present in the film from about 1% to about 70% by weight. The extracted substance from *cannabis* or hemp may exist in the form of an isolate, which is powder like and is light yellow in color. The extracted substance may also exist in the form of an emulsion without waxes and oils, oil, paste, liquid, resin, crystal, powder, or pulp.

The thin film may additionally include permeability enhancers in amounts from about 0.001% to about 10% by weight of the film and may be selected from the group of one or more calcium chelators, polycarboxylic acids, zonula occluding toxin, poly-L-arginine, chitosan derivatives, niacin, omega 3 or 6 fatty acids or other fatty acids, menthol, sodium caprate, sodium deoxycholate, dipotassium glycyrrhizinate, 25 furanocoumarins and grapefruit derivatives, bile salts, ethylenediaminetetraacetic acid (EDTA), tocopheryl polyethyleneglycol succinate (TPGS), derivatives thereof, and combinations thereof, or the like.

Since the CBD and THC have a very bitter taste, the film may also contain one or more taste masking agents or bitter blockers. The amount of the taste masking agents may range from about 0.001% to about 0.5% by weight of the film and may be selected from the group of kleptose, cyclodextrin, cyclodextrin derivatives, ginger, anise, cinnamon, peppermint, licorice, fruit juice, sweeteners, sucrose, glucose, fructose, mannitol, saccharin, aspartame, sucralose, *stevia* plant derivatives, honey, or any combination thereof.

The matrix containing the active agent may be formed from an edible polymer that is natural such as, but not limited to, methylcellulose, hydroxypropylmethylcellulose, ethylcellulose, sodium alginate, starch, chitosan, chitin, pullalan, agar, derivatives and/or combinations thereof. The matrix may also be formed from synthetic polymers including, but not limited to, hydroxyethylcellulose, cellulose acetate phthalate, hydroxypropyl methylcellulose phthalate, carboxymethyl ethylcellulose, hydroxypropylmethyl cellulose acetate succinate, polyvinyl acetate phthalate, maltodextrin, dextran, hydroxypropyl cellulose, sodium carboxymethyl cellulose, poly(methacrylic acid-co-ethyl acrylate), poly(methacrylic acid-co-methyl methacrylate), poly(methacrylic acid-co-ethyl acrylate), poly(methacrylic acid-co-methyl methacrylate), polyvinylpyrrolidone, polylactic acid (PLA), poly-L-lactide (PLLA), poly-D-lactide (PLDA), poly(lactic-co-glycolic acid) (PLGA), and mixtures thereof.

The matrix may further contain additional compounds selected from the group of a solubilizer, a thickener, a surfactant, a coloring agent, a flavorant, an effervescent agent, an antioxidant, a bioadhesive agent, a pH modifying agent, vitamins, minerals, a dietary supplement, one or more of different strains of cannabidiol from plants, anti-inflammatory substances, steroids, medicaments, cosmetic components, pharmaceutical, nutraceutical, or mixtures thereof.

The film of the present disclosure may be prepared from any method including, but not limited to, solution casting, spin coating, extrusion, calendaring, roll-pressing, microfabrication, molding jet printing, drop-on demand printing, dot, printing, etc. The resulting film product may have a thickness ranging from about 0.1 mils to about 30 mils.

Generally, the method of preparing a thin mucosally dissolvable film include the steps of: (a) providing an active agent, which is an extracted substance obtained from *cannabis* or hemp, and includes cannabinoids (CBD) or tetrahydrocannabinol (THC) in concentration of at least 90% and up to about 100%. (ii) dissolving the active agent in a solvent mixture; (iii) forming a homogenous emulsion of the active agent and solvent mixture at temperatures ranging from about 70° F. to about 380° F.; (iv) adding a sugar polymer and additives to the homogenous emulsion to form a modified emulsion; (v) casting the modified emulsion into a film, and (vi) drying the film.

The method may further include packaging the dried film with foils on each side to form a single packet.

DETAILED DESCRIPTION

The present disclosure is not limited in terms of the particular embodiments described in this application, which are intended as illustrations of various aspects only. Many modifications and variations can be made without departing from the scope of the invention, as will be apparent to those skilled in the art. Functionally equivalent methods within the scope of the disclosure, in addition to those enumerated herein, will be apparent to those skilled in the art from the following descriptions. Such modifications and variations are intended to fall within the scope of the appended claims. It is also to be understood that the terminology used herein is for the purpose of describing particular embodiments only, and is not intended to be limiting.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells.

Generally, the present invention is related to mucosally dissolvable film having an active agent. The "active agent" may include one or more substances, such as cannabinoids or cannabidiol (CBD) or tetrahydrocannabinol (THC) obtained from hemp and/or *cannabis*. The "active agent" may also include an extracted substance from hemp or *cannabis* such as the CBD or THC, in addition to other biologically active substances such as, but not limited to, drugs or medicaments, nutraceuticals, pharmaceutical that can alleviate a symptom in a subject in need thereof. In another aspect, the active agent refers to only the biologically active agents such as drugs or medicaments, nutraceuticals, pharmaceutical that can alleviate a symptom in a subject in need thereof.

The "films" or "wafers" or "sheets" can be any type of film that can be administered to a subject to provide the substance or mixture of substances from hemp or *cannabis* or other biologically active agents such as a medicament or a pharmaceutical or a nutraceutical. In one example, the films may be sublingual or orally dissolving films or mucosally dissolving films, that are edible and pharmaceutically acceptable. A "mucosally dissolvable film" refers to any thin film that allows an active agent to seep or absorb through the mucosal membrane of any mammalian subject. It is not the same as any oral film that is swallowed such that the film components, including the active agent, traverses the digestive tract of the subject. The mucosal transmission of the active agent in the present disclosure is enabled by the lipid based emulsion system and/or the penetration enhancers and buffer system employed during the preparation of the film. It will be appreciated that any other type of film may be used such as those that are allowed to dissolve or absorb in a mouth, vagina or rectum. The films of the present disclosure may also adhere to any mucosal tissue of a subject or may also adhere to skin of a subject.

Also, the present disclosure is related to methods of making emulsions having the substance or mixture of substances from hemp or *cannabis*, and use of the emulsions for making the mucosally dissolvable films.

Active Agents

The substance or mixture of substances may be obtained from hemp or *cannabis* in any form. That is, the one or more substances may be in any composition format, such as an oil or wax extract, or paste, any liquid format, resin, crystal, powder, isolate or pulp form. Previously, it has been found to be difficult to incorporate oils or extracts from hemp or *cannabis* into a uniform and consistent composition to prepare dissolvable films that can be reliably produced across batches. Typically, such sources of substances are very hydrophobic in nature, and thus do not mix or dissolve into water, thereby making it rather difficult to incorporate the oils or waxes into materials, such as dissolving films.

In this disclosure, the extracted substance or the active agent (e.g., CBD or THC) is the main constituent of the films described herein, wherein the active agent can exist as 0.1% to 90% of such obtained substances. Specifically, the extracted substance or active agent (e.g., CBD or THC) may be in a purified form such that the concentration of the CBD or THC is greater than 90%, greater than 95%, greater than 98% or greater than or about 99%. The purified substances, if used in the preparation of the film, may also be purchased from manufacturers. For example, the commercially available Elixinol 99.4% Hemp extract isolate, EX-513W contains 90-100% CBD and no THC and it may be suitable for the preparation of the film of the present disclosure. Similarly, an extract containing more than 90% of THC and little or no CBD may be purchased from CLEAR. It will be appreciated that using such high concentration of purified CBD is advantageous because, a film with a higher loading dosage can be prepared with lower amounts of purified substances. For example, a film formulation may include an extract from *cannabis* having at least 90% and up to about 100% CBD and may be present in the film from about 1% to about 70% by weight of the film. On the other hand, if less purified substances such as a raw extract from *cannabis* or hemp containing less than 35% CBD is used, then to achieve the same high loading dosage more than 90% of CBD may be needed in the film. Additionally, using higher concentrations such as >90% of CBD or THC isolate in a film of the present disclosure would prevent the bitter taste of flavonoids or other raw plant materials from *cannabis* or hemp. It will be understood that the extracted substance may also be used in a less purified form such that the concentration of CBD or THC is less than about 90%, about 70%, about 60%, about 50%, about 30%, or about 15%.

The agent (e.g., substance from hemp and/or *cannabis*) may be prepared into an emulsion that if formed into a film, such as an orally dissolving film, the agent may be present from less than 1% to greater than 60% by weight of the film.

The substance obtained from hemp or *cannabis* may be a wax or oil or paste or other format and may have a concentration from about 0.1% to about 90%. Such composition can be the source of the substance or mixture of substances. CBD wax may come from industrial hemp or *cannabis*, with CBD ranging in a concentration of 0.1% to 90%, which is usually a viscous extract containing various amounts of CBD, and depending on extraction method and material source (industrial hemp or *cannabis*) may contain varying amounts of additional plant material such as chlorophyll, terpenes or THC. CBD extract may be extracted using various methods, one method is to use carbon dioxide which may prevent additional unwanted substances in the final product. Other methods that may be used to extract CBD from hemp include ethanol and oil extraction. CBD oil may come from industrial hemp or *cannabis*, with CBD ranging in a concentration of 0.1% to 90%, which is typically less viscous than waxes, oils may be extracted in various ways and contain varying amounts of CBD and other plant extracts such as chlorophyll, terpenes and THC. CBD oil may be extracted using carbon-di-oxide in a similar way to the generation of CBD wax. Additionally, ethanol or oil may be used to create a CBD oil.

The commercially available CBD oil such as ELIXINOL 35% CBD Hemp Oil, EX-AMBR-21 (Raw and decarbed) which contains 31-5% to 38.5% CBD and 1.05% to 1.2% THC or ELIXINOL 4% CBD Hemp Oil, EX-213 (Raw and Decarbed) containing 3.6% to 4.4% CBD and 0% THC or ELIXINOL 17.4% CBD Hemp Oil, EX-913 (Raw and decarbed) containing 15.7% to 19.1% CBD and only a trace amount of THC (0.51%) may be used in the preparation of the films of the present disclosure.

Figure 1:
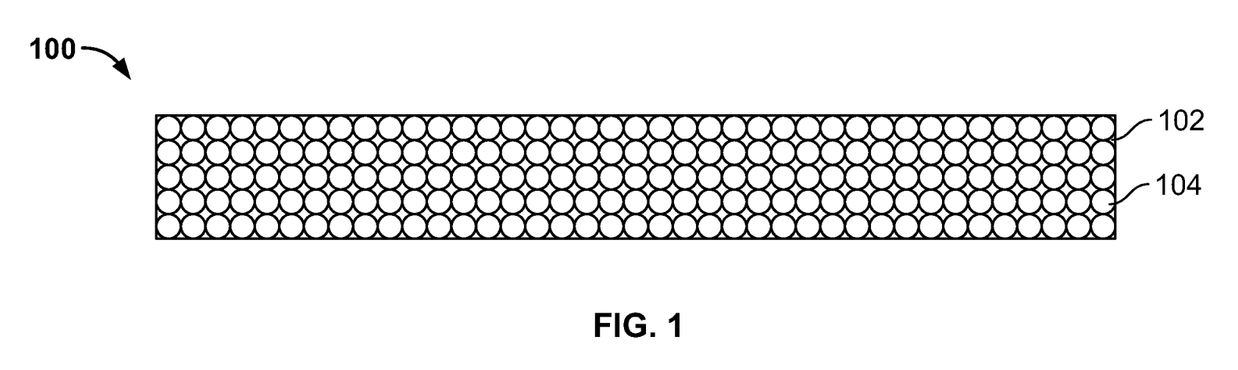
FIG. 1 is a diagrammatic representation of a thin film showing the active agent dissolved in the matrix.
Figure 2:
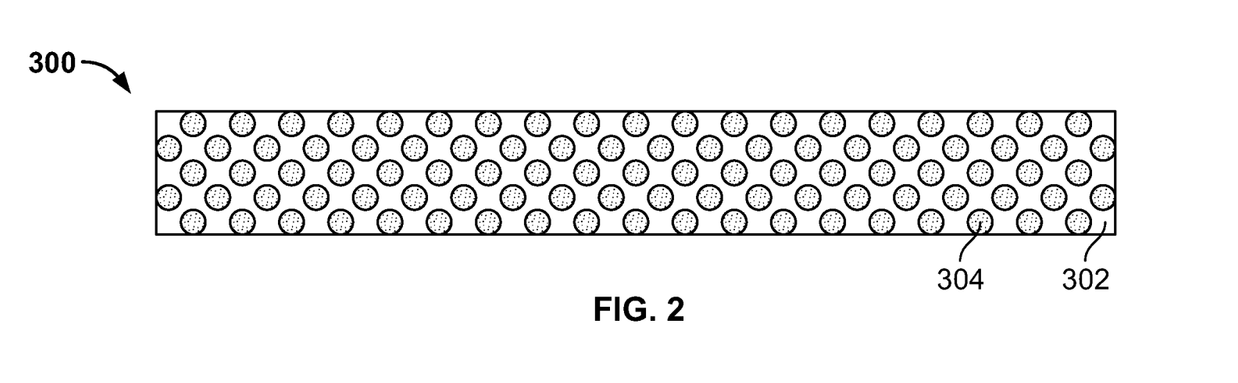
FIG. 2 is another embodiment of the film with insoluble active agent impregnated in the film matrix.

The active agent 104 or drug may be used as fine particles (shown in FIG. 1) or the drug can be agglomerated alone with an agglomerating agent into particles. The resulting particles may then be suspended in the film sheet carrier matrix (e.g., polymer matrix). While some drugs may be in a particle format that is suspended 304 in the carrier matrix 302 as shown in FIG. 2, some drugs can be dissolved in the carrier matrix (see FIG. 1). The particles can be micro- and/or nanoparticles. The particles can be microspheres, liposomes, micelles, or other agglomeration of molecules. When the active agent is in a nanoparticle size or single molecule, such as less than about 500 nm, it may be combined with a water-soluble polymer composition to form a self-supporting film in accordance with the present disclosure. However, the CBD and/or THC may be in the form of particles, such as in a powder.

The film may be prepared to have a specific amount of biologically active agent, such as a specific amount of drug. The amount of drug included should be consistent across a number of batches so that the ingestible unit can achieve regulatory compliance. Accordingly, the method of preparing an ingestible unit can include: preparing a composition having a biologically active agent at a defined amount; forming the composition into a discrete sheet to have the biologically active agent at a defined amount; and including the discrete sheet in a package. The method may also include: determining a dose of a biologically active agent to be included in a film. Drug loading into sheets may be up to about 70% by weight of the sheet, and often up to about 50% by weight. The amount of drug in each sheet can be calculated before or after shaping the individual sheets or ingestible unit into the size and shape of the dosage form. The amount of drug lost during processing can also be taken into account in order to design the ingestible units and select the appropriate number of sheets to arrive at the predetermined dose.

However, it should be recognized that a single sheet may be suitable for the entire dose of an ingestible unit. The same methodologies can be performed when the ingestible unit includes two or more different biologically active agents. Moreover, this methodology can be used for determining the amount of any agent or ingredient described herein.

Other Components of the Film

In addition to the active agents obtained from *Cannabis* or Hemp and/or a biological drug, the film of the present disclosure may also contain permeability or penetration enhancers or absorption enhancers to improve the absorption of the active agent by the mucosal tissues of a subject, and taste-masking agents or bitter blockers to mask the bitter taste of CBD or THC. The penetration enhancers may include compounds such as, but not limited to, calcium chelators such as EOTA, polycarboxylic acids, zonula occluding toxin, poly-L-arginine, chitosan derivatives, niacin, omega 3 or 6 fatty acids or other fatty acids, menthol, sodium caprate, sodium deoxycholate, dipotassium glycyrrhizinate, 25 furanocoumarins and grapefruit derivatives, bile salts, ethylenediaminetetraacetic acid, tocopheryl polyethyleneglycol succinate (TPGS), derivatives thereof, and combinations thereof, or the like. These penetration or absorption enhancers may be present in an amount ranging from 0.001% to about 10% by weight of the film. The preferred amount of penetration enhancer in the film may range from about 0.1% to about 3% by weight of the film.

The taste-masking agent on the other hand, may be selected from kleptose, cyclodextrin, cyclodextrin derivatives, ginger, anise, cinnamon, peppermint, licorice, fruit flavoring, citric acid, fruit juice, sweeteners, sucrose, glucose, fructose, mannitol, saccharin, aspartame, sucralose, *Stevia* plant derivatives, honey, derivatives thereof, and combinations thereof. The amount of the taste-masking agents or bitter blockers in the film may range from about 0.001 to 5% by weight of the film, preferably from 0.001 to 0.5% by weight of the film.

The film may further include one or more components in the matrix such as, but not limited to, a film-forming agent; a filler; a plasticizer; a taste-masking agent; a coloring agent; a solubilizing agent; an effervescent agent; an antioxidant; an absorption enhancer; a disintegrating agent; a pH modifying or buffer agent; a surfactant; a complexing agent; a bio-adhesive agent; a sheet adhesive; an identifying agent; an anti-counterfeiting agent; a tracking agent; transporter inhibitor agent; transporter inducer agent; emulsifying agent, self-emulsifying system agents; crystallization inhibitor; crystallization promoter; super-saturation promoting agent; antimicrobial preservative; catalyst; chelating agent; particles; organoleptic agent; flavoring agent; scent agent; identifying device; and/or anti-counterfeiting device. These types of ingredients can be exemplified by substances that are commonly used for pharmaceutical compositions or other ingestible compositions. Preferably, these types of ingredients are defined as generally recognized as being safe (GRAS) by a government agency, such as the U.S. FDA. In one embodiment, the ingredients can be defined as being approved by a select committee on GRAS substances (SCOGS), such as which can be found at the U.S. FDA website, which is incorporated herein by specific reference in its entirety, specifically included is the GRAS and SCOGS ingredients.

The film of the present disclosure may also be prepared from agents selected from methylcellulose, hydroxypropylmethylcellulose, ethylcellulose, sodium alginate, poly (methacrylic acid-co-ethyl acrylate), poly (methacrylic acid-co-methyl methacrylate), starch, 30 polyvinylpyrrolidone, polylactic acid (PLA), poly-L-lactide (PLLA), poly-D-lactide (PLDA), poly (lactic-co-glycolic acid) (PLGA), chitosan, chitin, pullulan, derivatives thereof, and combinations thereof. The plasticizer when used in the preparation of the film may be selected from glycerine, triacetin, triacetyl citrate, polyethyleneglycol, mineral oil, myglyol, derivatives thereof, and combinations thereof.

The film compositions may further include food colorants, such as carotenoid compounds and FD&C red, green, yellow, and blue, or the like. The solubilizing agent can be selected from polyvynilpyrrolidone, polyvinylcaprolactam-polyvinylacetate-polyethyleneglycol copolymer, fatty acids, castor oil, cyclodextrins, polyethyleneglycol, glyceryl distearate, lecithin, monoglycerides, diglycerides, triglycerides, propylene glycol monostearate, Labrafils (e.g., oleoyl macrogol-6 glycerides, oleoyl polyoxyl-6-glycerides, linoleoyl macrogol-6 glycerides, linoleoyl polyoxyl-6 glycerides, lauroyl macrogol-6 glycerides, lauroyl polyoxyl-6 glycerides), Labrasols (e.g., caprylocaproyl macrogol-8 glycerides, caprylocaproyl polyoxyl-8 glycerides), Solutols (e.g., polyoxyethylene esters of 12-hydroxystearic acid), Soluplus (e.g., polyvinyl caprolactam-polyvinyl acetate-polyethylene glycol graft co-polymer), derivatives thereof, and combinations thereof. Soluplus can also be used as a film-forming agent.

The effervescent agent may be selected from sodium carbonate, bicarbonate, potassium carbonate, calcium carbonate, citric acid, malic acid, tartaric acid, adipic acid, fumaric acid, derivatives thereof, and combinations thereof.

The antioxidant, if present in the film, may be selected from tocopherol, vitamin E, resveratrol, ascorbyl palmitate, tert-butylhydroquinone, resveratrol, nordihydroguaiaretic acid, cysteine, propyl gallate, octyl gallate, 3-tert-butyl-4-hydroxyanisole, butylated hydroxytoluene, ascorbic acid, derivatives thereof, and combinations thereof, or the like.

The disintegrating agent may be selected from croscarmellose sodium, sodium starch glycolate, insoluble polyvinylpyrrolidone, carboxymethylcellulose, derivatives thereof, and combinations thereof, or the like.

The film may also include pH modifier or buffer agent selected from sodium carbonate, magnesium carbonate, calcium carbonate, sodium hydroxide, potassium hydroxide, ascorbic acid, citric acid, succinic acid, fumaric acid, derivatives thereof, and combinations thereof.

The surfactant in the film may be selected from sodium lauryl sulfate, poloxamers, sorbitan esters, polysorbates, sorbitans, stearic acid, derivatives thereof, and combinations thereof.

The complexing agent, if present in the film, may be selected from cyclodextrins, calcium glycerophosphate, dodecyl 2-(N,N-dimethylamino) propionate, zinc, dextran, pectin, copper acetate, sodium deoxycholate, calcium, magnesium, derivatives thereof, and combinations thereof.

The bio-adhesive agent, if present in the film, may be selected from gelatin, starch, glycoproteins, proteins, carbohydrates, mucopolysaccharides, derivatives thereof, and combinations thereof.

The sheet adhesive, if present in the film, may be selected from polyvinylpyrrolidone, polyvinyl alcohol, polyvinyl acetate, confectionary glue, starch, derivatives thereof, or combinations thereof.

The tracking agent, identifying agent, or anti-counterfeiting agent, if present in the film, may be selected from fluorescein, rhodamine, succinimidyl esters, maleimide activated fluorophores, fluorescent dyes, fluorescent particles, infrared active particles, near infrared active particles, metallic nanoparticles, polymeric particles, silica based nanoparticles, SERS (Surface Enhanced Raman Spectroscopy) particles, raman active particles, derivatives thereof, and combinations thereof.

The osmotic agent, if present in the film, may be selected from mannitol, osmitrol, dextrose, sucrose, fructose, sodium chloride, potassium chloride, xylitol, sorbitol, lactose, potassium phosphate, derivatives thereof, or combinations thereof.

The transporter inhibitor, if present in the film, may be selected from elacridar, zosuquidar, glibenclamide, quinaxoline derivatives, phenylalanine, arginyl naphthylamide, grapefruit derivatives, furanocoumarins, derivatives thereof, and combinations thereof. The transporter inducer, if present in the film, may be selected from xenobiotics, diallyl sulfide, dexamethasone, derivatives thereof, and combinations thereof.

The emulsifying agent, if present in the film, may be selected from tocopheryl polyethyleneglycol succinate (TPGS), Cremophor (e.g., non-ionic polyethoxylated detergents), Lutrol (e.g., polyethylene glycol), Poloxamers (e.g., polyethylene-polypropylene glycol), cholesterol, octyldodecanol, polyoxylglycerides, derivatives thereof, and combinations thereof.

The self-emulsifying system may be selected from Labrasol, Labrafil, Cremophor, Pluronics, Lutrol, poloxamers, polysorbates, ethyl linoleate, mono- and diglycerides of capric and caprylic acids, tocopherol acetate, Solutol, soybean oil, tocopheryl polyethyleneglycol succinate (TPGS), Capmuls, derivatives thereof, and combinations thereof, or the like.

Crystallization inhibitors, if present in the film, may be selected from polyvinylpyrollidone, hydroxypropylmethylcellulose, silicon dioxide, dextrins, dextrans, bile acids, sterols, polysebacic anhydride, derivatives thereof, and combinations thereof.

The supersaturating promoting agent, if present in the film, may be selected from hydroxyproylmethylcellulose, hydroxypropylmethylcellulose acetate succinate, polyvinylpyrollidone, derivatives thereof, and combinations thereof.

The antimicrobial preservative, if present in the film, may be selected from benzoic acid, sodium benzoate, methyl paraben, propyl baraben, butyl paraben, sorbic acid, propionic acid, dehydroacetic acid, derivatives thereof, and combinations thereof. The catalyst may be selected be heavy metals selected from Ni, Cr, Mn, Zn, Fe, or combinations thereof, or the like.

An organoleptic agent may be a flavorant or scent, such as selected from vanilla, bubble gum, fruit flavor, mint, chocolate, licorice, marshmallow, peanut butter, aspartame, sucralose, sucrose, glucose, citric acid, *stevia* plant, derivatives thereof, or combinations thereof. The organoleptic agent for a veterinary embodiment can be selected from glutamates, chicken flavor, umami flavoring, beef flavor, fish flavor, or the like. The chelating agent, if present in the film, may be selected from disodium edetate, EDTA, pentetic acid, derivatives thereof and combinations thereof.

Starches such as corn starch, potato starch, pregelatinized and modified starches thereof, cellulosic agents such as Act-di-sol, montmorrilonite clays including cross-linked PVP, sweeteners, bentonite and VEEGUM™, microcrystalline cellulose, alginates, sodium starch glycolate, gums such as agar, guar, locust bean, karaya, pecitin and tragacanth may also be included in the film. Disintegrants may comprise up to about 20 weight percent and preferably between about 2 and about 5 percent of the total weight of the composition.

The film may also include surfactants such as sodium lauryl sulfate, sodium dodecyl sulfate and tween; bile salts such as sodium taurocholate; fatty acids such as oleic and linoleic acid; and non-surfactants such as AZONE and dialkyl sulfoxides.

Coloring agents may also be present in the film and could include titanium dioxide, and dyes suitable for food such as those known as F.D. & C. dyes and natural coloring agents such as grape skin extract, beet red powder, beta-carotene, annato, carmine, turmeric, paprika, etc. The coloring agent, if present in the film, may range from about 0 to about 2.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.5 to about 3.0 by weight based upon the weight of the composition. Particularly preferred flavors are the grape and cherry flavors and citrus flavors such as orange.

Vitamins may be included and refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), nicotinamide adenine dinucleotide (AND), nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes. A mineral may be used in the films, and refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The film may also include a dietary supplement, which is a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

The film may further include binders such as but not limited to acacia, tragacanth, gelatin, starch, cellulose materials such as methyl cellulose and sodium carboxymethyl cellulose, alginic acids and salts thereof, polyethylene glycol, guar gum, polysaccharide, sugars, invert sugars, poloxomers (PLURONIC F68, PLURONIC F127), collagen, albumin, gelatin, cellulosics in nonaqueous solvents, and combinations of the above and the like. Other binders include, for example, polypropylene glycol, polyoxyethylene-polypropylene copolymer, polyethylene ester, polyethylene sorbitan ester, polyethylene oxide or combinations thereof and the like. Hydrophobic binders can also be used in the invention.

Film and its Properties

It will be understood that the term "film" according to this disclosure includes thin films and sheets, in any shape, including rectangular, square, or other desired shape. The films described herein may be any desired thickness and size suitable for the intended use. For example, a film of the present disclosure may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution 5 of components through the application of controlled drying of the film.

Furthermore, the films of the present disclosure may have a substantially uniform thickness because it is known that absence of a uniform thickness detrimentally affects uniformity of component distribution throughout the area of a given film. Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e., drying oven or tunnel, to communicate through feedback loops to control and adjust the opening in the coating apparatus, resulting in control of uniform film thickness. Alternatively, the thickness of the film can also be controlled by manual measurement during the production process to achieve the desired thickness of the film.

The film sheets of this disclosure may have various thicknesses depending on the ingredients and matrix materials. The thickness of a sheet can range from about 100 nm to about 500 microns. Nano-scale sheets can range from about 100 nm to about 1000 nm, from about 200 nm to about 900 nm, from about 300 nm to about 800 nm, from about 400 nm to about 700 nm, or from about 500 to about 600 nm. The micron-scale sheets can range from about 1 micron to about 500 microns, from about 10 microns to about 250 microns, from about 20 microns to about 200 microns, from about 30 microns to about 150 microns, from about 10 microns to about 125 microns, from about 50 microns to about 100 microns, from about 60 microns to about 90 microns, or from about 70 microns to about 80 microns. However, it should be recognized that the sheets can have any thickness that allows for preparation into an ingestible unit as described herein. In one example, each discrete sheet has a thickness less than 50 microns.

The film sheets may exist as thin strips with an area of roughly 1 in² and 4 mils thick, plus or minus 1%, 5%, 10%, 15%, 20%, 25% thereof. The dimensions of such film sheets limit the total amount of drug that can be contained therein. For example, CBD can be provided in doses of 0.1 mg, 1 mg, 2 mg, 3 mg and 4 mg and 8 mg and 10 mg or up to 60 mg. This dosage film weight amount can be available in doses of 100 mg, 200 mg, or even 30 greater. Now, the film sheets can be prepared with a specific or maximum amount of agent contained therein.

The films can have various configurations and formats. The films may have a larger width and length compared to thickness. This provides a top surface and a bottom surface with a significant cross-sectional profile, but is relatively thin in order to be a sheet. The sheets may be films, lamina, laminates, wafers, or other thin-body structures. The films may range from about 100 nanometers to many microns in thickness. A sheet can be a lamina or a laminate of a plurality of lamina. The lamina can be a layer that is combined with other lamina layers into a laminate. While the discrete sheets are described to be combined into laminate structures, the individual sheets themselves can be prepared as laminates from one or more types of thin lamina. The thin lamina can be a thin plate or layer of material, which often is of a sub-micron size. The lamina can be prepared into a laminate and used as a sheet. The sheet can also be prepared as a wafer, which can be a thin member, such as a thin disk, and may be a dried paste, gelatin adhesive paper, or the like. Also, the wafer may be a thin sheet enclosing or containing a powder or particles, where the powder or particles can be a biologically active agent.

The film sheets can be shaped while being formed or shaped after being set. The laminates of the film sheets can also be cut into a specific shape before or after the film sheets are laminated together. The shaping can include cutting, stamping, laser-shaping, or any other method of cutting a thin film or a stack of films.

In one example, the thin film sheets can be edible polymer films, such as those that dissolve in the mouth. Such edible polymer films, which can be for delivery of pharmaceutical products, are commercially available. Widely-known examples of the edible polymer films include the Listerine® PocketPaks strips sold as a dry, portable breath-refreshing product, the Gas-X® peppermint-flavored thin strips containing simethicone as the active pharmaceutical ingredient (API), and the first prescription pharmaceutical film strip, Zuplenz®, containing ondansetron as the API, which was approved by the U.S. FDA in 2010 for the treatment of nausea following chemotherapy for example. These individual thin film sheets are prepared for individual consumption. These thin film sheet products are designed as orally disintegrating films.

The film of the present disclosure may be divided into equally sized units having substantially equal amounts of each compositional component present. This advantage is particularly useful because it permits large area films to be initially formed, and subsequently cut into individual units without concern for whether each unit is compositionally equal. For example, the films of the present disclosure have particular applicability as delivery systems for agents from hemp and/or *cannabis* because each film unit will contain the proper amount of the agent. The films may also have particular applicability as ingestible films, which are dissolved in the mouth of the user, either rapidly or over a controlled period of time. They may also be used for systemic administration of agents by applying the films to oral or vaginal mucosal surfaces.

A self-supporting film dosage composition may include at least one carrier or matrix (e.g., polysaccharide (pullulan) or polymer), and at least one active agent (e.g., substance from hemp and/or *cannabis*). The agent may be a small-scale particle such as a microparticle or a nanoparticle, or individual molecules.

Emulsion and Use of the Same in the Preparation of a Film

The active agent (e.g., substance from hemp and/or *cannabis*) may be prepared into an emulsion that if formed into a film, such as an orally dissolving film, the agent may be present from less than 1% to greater than 60% by weight of the film.

The agent may be in a purified agent, such as greater than 90%, 94%, or 99% in a crystal, isolate, or powdered form. The films and methods of preparing the emulsion or film can specifically exclude the use of extracts, waxes or oils from hemp or *cannabis*. Instead, such extracts, waxes or oils from hemp or *cannabis* can be ultrapurified into the powdered format described herein, which allows for accurate dosing of the agent in the emulsion and resulting film. The powdered agent can be obtained or prepared before inclusion in the emulsion. The powdered agent can include CBD and/or THC or other components from hemp or *cannabis* described herein, such as a crystalline form. The crystals can be grainy and in a powder.

Figure 4:
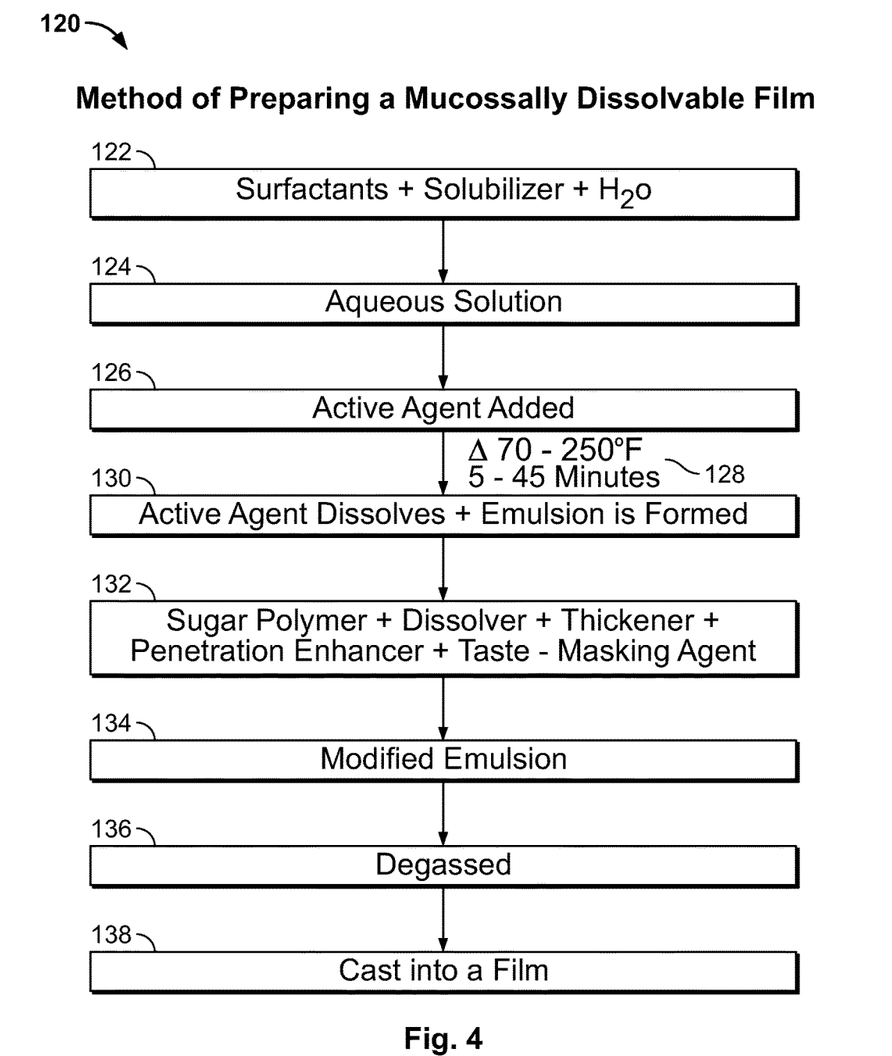
FIG. 4 illustrates a method for preparing an oral film, in various embodiments.

The general method 120 for the preparation of the film is shown in FIG. 4 and ingredients used in the preparation of the film, in an exemplary embodiment, is shown in Table 1 below.

| Ingredients | Percent of Strip | Amount | Mass/batch |
|---|---|---|---|
| Active | | (in mg/strip) | |
| CBD Isolate | | 12-70 | 12000-70000 |
| Matrix | | in mg/strip | |
| Pullalan | | 24-55 | 2400-5500 |
| Sucralose | | 1.5-3 | 150-300 |
| Guar gum | | 2.5-4 | 250-400 |
| Pectin | | 2-5 | 200-400 |
| Liquids | | in mL | mL/batch |
| Water ratio | 2.25 | | 25-50 |
| Vanilla | | 15 | 3-15 |
| Masking agent | | 5 | 0.8-5 |
| Permeability enhancer (menthol) | | 10 | 1-10 |
| Polysorbate | | 10 | 1-10 |
| Glycerin | | 5 | 0.4-5 |
| Colorant (Yellow) | | 2 | 0.6-2 |
| TOTAL | | 47 | 47 |

The method shows that a powdered agent is first prepared into an emulsion. The emulsion may be prepared from a surfactant (e.g., polysorbate or the like) and a solubilizer 122

(e.g., glycerin or the like) mixed together in an aqueous solution (e.g., water) 124. The agent is added to the surfactant, solubilizer, and water 126 to form the emulsion 130. Various emulsion preparation techniques can be used in the process, such as sonication, vibration, mixing, or the like. The composition having the surfactant and solubilizer with the agent can be heated at temperature ranges of 70° F. to 250° F. (128), or 100E-170° F., or about 120° F. for a period of 5-45 minutes, or 10-35 minutes or about 30 minutes to dissolve the agent and form the emulsion 130. It will be appreciated that the use of techniques such as vibration, vacuum and heat also aids in the efficient removal of air bubbles from the emulsion leading to a final homogenous emulsion. A suspension may also be formed. The emulsion may then be treated (132) with a sugar (e.g., saccharide or the like) or sugar polymer (e.g., polysaccharide or the like), such as pullulan or the like. Additionally, a dissolver (e.g., pectin or the like) may be introduced into the emulsion. A thickener (e.g., guar gum or the like) may also be introduced into the emulsion. A taste modifier, such as a sweetener (e.g., sucralose or the like) and a penetration enhancer may also be introduced into the emulsion. Other ingredients, such as flavoring agents (e.g., natural or artificial) or coloring agents (e.g., natural or artificial) may be introduced into the emulsion. After modifying the emulsion with one or more of the above-referenced modifiers, the resulting modified emulsion 134 may be prepared into the film having the agent.

The modified emulsion may then be degassed 136 prior to forming the film to release any trapped air in the emulsion. The degassing can be performed in open air or with vacuum; however, open air degassing without vacuum may be preferred to avoid loss of volatile substances from the hemp and/or *cannabis*. The modified emulsion can be introduced in a vessel and then cast into a film 138.

Further processing of the emulsion may include any processing approach that can result in a film. Examples of such processing may include extrusion (FIG. 6), solution casting box apparatus (FIG. 5), reverse roll coating casting, and other solution casting apparatus' known to those skilled in the art of solution casting. The modified emulsion can be passed between rollers (e.g., casting rollers), and rolled onto a substrate at the desired wet gauge thickness. The substrate can be a wax or silicone coated substrate that allows the film to be peeled therefrom once the film is stable. The rollers can be adjusted to change the gap there between to change the wet gauge thickness of the film. Once on the substrate, the film can be cured and solidified, such as by heating. In one example, the film on the substrate can be passed through a heater (e.g., infrared heater) with air flow to provide convection heating, which is regulated to remove moisture from the film. The film can be formed in this matter to inhibit rippling or other unfavorable characteristics, and may avoid blistering. Good throughout heating and curing can produce the desired film.

The active (e.g., pure powdered CBD or THC) may be added to a polysorbate and glycerin mixture and heated up just a little bit to get the active to dissolve. The glycerin is used as a solvent, and provides flexibility in the film. The polysorbate is used as a surfactant and creates a suspension when added to water and provides a suspension of CBD. Pullulan is then added, which as a sugar polymer forms into a matrix and provides the final emulsification. So the combination of the polysorbate, the Pullulan and the glycerin allow the CBD and/or THC to be dissolved or suspended into water uniformly as an emulsion. The Pullulan locks the active into sugar matrix and the entire solution becomes a uniform homogenous emulsion. Additional additives such as pectin and guar gum and sucralose may be added. The guar gum is used to thicken the solution which is helpful for the casting process. The pectin is used because it provides good dissolvability for the film and some structural properties. The sucralose is used as a sweetener and flavoring. Optionally, we can add any desirable flavors to improve the taste and food coloring agent for aesthetics. The emulsion having the polysorbate, Pullulan and glycerin allows the CBD and/or THC to be suspended uniformly and homogenously so that the right amount of CBD and/or THC is included in each film strip.

The method of preparing an emulsion composition may also include providing an aqueous-based emulsion and converting the aqueous-based emulsion into a non-aqueous dry emulsion, wherein the dry emulsion is in the form of a self-supporting film. The method further includes dissolving the film with an aqueous solvent, thereby reforming the aqueous-based emulsion. Another method of preparing an emulsion composition includes providing a solid water soluble polymeric film having dispersed therein an active agent; and adding water to dissolve the film, thereby forming an emulsion.

Moreover, the disclosure also provides a method of preparing a film for delivery of an active. The method includes preparing a composition including at least one water soluble polymer; a polar solvent (water); and an emulsion composition that includes the active; and forming a film from the prepared composition. The method further includes drying the film by a process whereby the active become dispersed within the film. Also provided is a method of preparing a water reconstitutable emulsion composition. The method includes preparing a composition including at least one water soluble polymer; a polar solvent; and an emulsion composition. The method also includes drying the composition to form a dry emulsion including active agent within a solid water soluble polymeric matrix.

In one embodiment, the film can be prepared to have a specific amount of biologically active agent, such as a specific amount of drug. The amount of drug included should be consistent across a number of batches so that the ingestible unit can achieve regulatory compliance. Accordingly, the method of preparing an ingestible unit can include: preparing a composition having a biologically active agent at a defined amount; forming the composition into a discrete sheet to have the biologically active agent at a defined amount; and including the discrete sheet in a package. The method may also include: determining a dose of a biologically active agent to be included a film. Drug loading into sheets can be up to about 70% by weight of the sheet, and often up to about 50% by weight. The amount of drug in each sheet can be calculated before or after shaping the individual sheets or ingestible unit into the size and shape of the dosage form. The amount of drug lost during processing can also be taken into account in order to design the ingestible units and select the appropriate number of sheets to arrive at the predetermined dose. However, it should be recognized that a single sheet may be suitable for the entire dose of an ingestible unit. The same methodologies can be performed when the ingestible unit includes two or more different biologically active agents. Moreover, this methodology can be used for determining the amount of any agent or ingredient described herein.

The emulsion technology used to prepare the film of the present disclosure has a greater advantage in terms of accurate dosing of the film. Specifically, the use of a lipid or fat based emulsion system allows for more accurate dosing that may vary only by ±2% or lower. On the other hand, the dosing of prior art films may vary widely by >3% or >5% or >10% or >50%. This is because the prior art compositions rely on simple extracts from *cannabis* or hemp that contain oils, waxes and other plant raw materials that hinder the preparation of a homogenous emulsion or they may dissolve the CBD or THC in alcohol or fat and then place into an emulsion to prevent separation, or the active agents leach out of the film during the process. All these may result in very inaccurate dosing of the active agent in the film.

Figure 3:
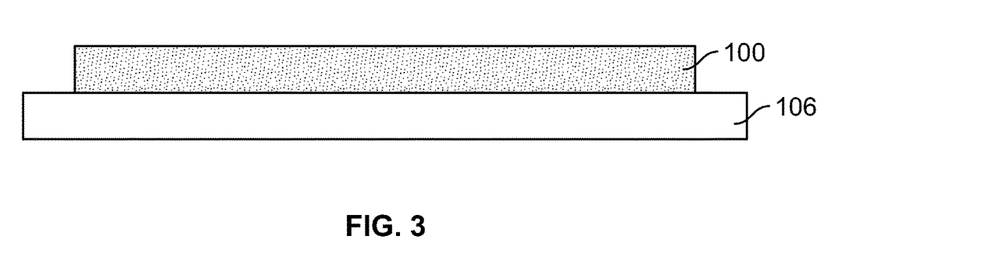
FIG. 3 is a diagrammatic representation of the film cast on a wax or silicon substrate.
Figure 3A:
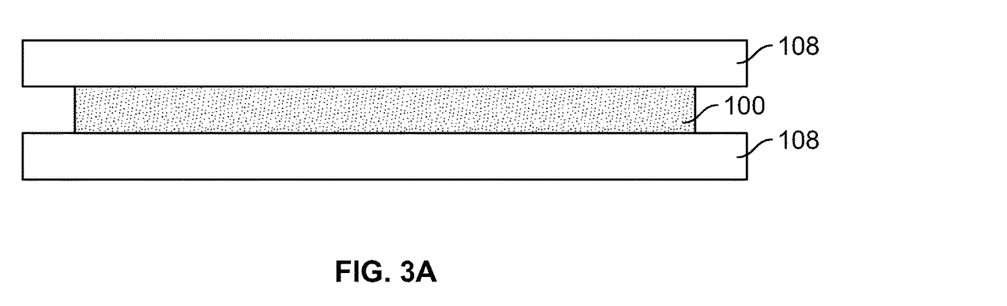
FIG. 3A is a diagrammatic representation of the film that is disposed between two protective foils.
Figure 3B:
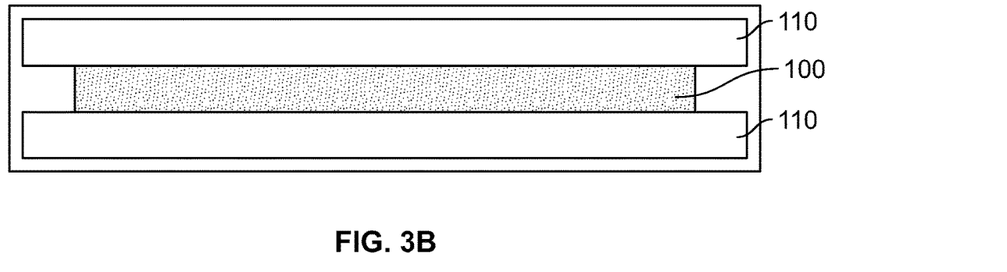
FIG. 3B is a diagrammatic representation of the film that is disposed between two protective foils combined with poly layers creating individual sealed pouch package.

Once the film is formed over a substrate such as wax or silicone (FIG. 3), the film may be separated from the substrate. Such separation can include peeling, slicing, or parting the film from the substrate. The film may then be cut into desired sizes, such as the sizes described herein. The cut film may then be packaged for use. The packaging may be for individual films or in a dispenser that dispenses single films from a film stack such as varying the dimensions of the individual film dose strip. In one example, the individual film can be packaged between two foil layers (FIG. 3A), and then placed into an individual package. To use, a user can open the package, remove the foil layers, and place the film in the mouth. Vaginal or rectal administration may also be performed.

In one example, the film may be 4 mils thick and 1 inch by 1 inch square. If prepared properly, this configuration can be a 100 mg film having 10 mg active, such as CBD and/or THC. However, the active can be formulated to be up to about 60% of the film to provide 60 mg active. Also, a 60 mg per 130 mg film may also be prepared. Also, a prepared 10 mg CBD film will be less than or more than 100 mg. The individual films may be evaluated by weight or have other characterizations to accurately determine the amount or concentration of the active in the film. A film does not have a set ratio of active to inactive ingredients. (e.g., A film may contain 1 mg of active with a total weight of 100 mg.)

It should be recognized that the substances described above may be substituted with other equivalent substances. For example, starches may be used.

Preparation of a Film and Film Casting

The emulsion prepared as described above may be taken from the existing mixing vessel or put into a run tank vessel and then is cast on a line. The process may use a very unique reversal roll method between two stainless steel rollers. The casting roller in the front dictates the speed of the line. A wax coated carrier paper or silicone paper or other coated or uncoated paper or other material starts at the casting box and can be used to carry the film forming composition through the oven. The film is cast at the desired thickness to get a final thickness, and it goes through an infrared heater system, which has convection air flowing through from an exhaust fan to help draw the moisture off the film. Good convection air flow in the tunnel that keeps the moisture coming off at a constant rate and as long as the line speeds matched with the temperature settings correctly, the process provides good uniform drying that doesn't have underneath wet spots under the film top layer.

The film is cast at the desired wet thickness to get the desired final thickness of the partially or completely dehydrated film. The film is dehydrated as it is carried through an infrared heater system, that has convection air flowing through from an exhaust fan to help draw the moisture off the film. By generating adequate convection air flow through the oven tunnel, moisture is evaporated from the film at a constant rate. When the speed of drying and the temperature settings are sufficiently matched, the end result is an evenly dried film. This controlled heating and uniform heat application prevent the film from drying at an uneven pace which may cause a dried exterior covering wet film. The dried film is collected on a spool containing the carrier paper (or other carrier medium) and the film at the end of the oven system. The carrier paper and film are then transferred to another machine to perform the cuts that create one inch bobbins. The bobbin size may vary to accommodate various dosages. From the cutting machine, a bobbin is then transferred to a packaging machine. The packaging machine peels the film away from the carrier paper and then cuts individual strips of film and places each piece between two foil layers. The foil is then heat sealed on all sides to protect the individual films.

Also, the dried film can be obtained at the other end of the oven on a roll system, to provide a finished roll of dissolving film on top of the wax or silicone paper. The paper having the film goes through a slitting process from the bulk roll into bobbins ranging from widths of ½" to 1¾" inches depending on the dosage level, and then that bobbin goes onto a packaging machine that individually cuts the film to size based on the dosage amount. The cut film gets packed between two protective foil layers, and the foils are heat sealed around the film, and then individually packed.

The following protocol is only one example of how to make the films described herein. The emulsion mixture used for film formation is prepared as such. The reaction vessel is set to a temperature of 90° F. through the use of recirculated water through the water jacket on the reaction vessel. Deionized water is added to the vessel, and the mechanical stirrer is set to approximately 300 RPM (this can vary). From this point on the reaction vessel should always be sealed to ensure that minimal amounts of water and volatiles escape, and to ensure that no contaminants enter the reaction vessel, only remove the stopper to add ingredients. The active compound, in this case purified CBD crystal isolate powered are used. In a separate glassware/container/vessel, the active compound, in this case purified CBD, is added to a mixture of polysorbate (or other surfactant/emulsifier) and vegetable glycerin (or other carrier solvent/softening agent) and the mixture is mixed until the active compound is dissolved. Heat, up to 500° F., or preferably up to 380° F. can be applied to the mixture to aid in the formation of an even mixture with the active compound dissolved and/or distributed evenly. The flavoring agents can also be included into this solution to help increase the volume and aid in dissolvability, or the flavoring agents can be added directly to the reaction vessel. Assuming that flavoring agents were also added to the mixture of active compound, vegetable glycerin, and polysorbate, the entire mixture is then slowly added to the reaction vessel containing water up to this point and being stirred via mechanical stirrer. Continue to stir mixture to ensure uniform distribution of added solution and thus the formation of a homogenous emulsion. Next, the pullulan is added slowly to thicken the solution and lock the homogenous mixture into a polysaccharide matrix.

Once the mixture is uniform and all of the pullulan (or other polysaccharide or film former) has been added, the remaining thickening agents can be added, and at this point the stirring might need to be increased to 500 RPM (this can vary). The pectin (or other thickening agent) is added to the mixture, and then guar gum (or other thickening agent) is added. Continue to stir the solution to ensure a homogenous mixture. Add the sucralose (or other sweetener) to the mixture and ensure that all of it is mixed into solution. Finally, the food coloring is added to desired color, and the mixture continues to stir to evenly distribute the color.

At this point the solution contains a good amount of air in solution due to mixing and two options are available. Option 1, the stirring is slowed down and the entire reaction vessel is placed under vacuum to pull the air from the mixture, and is kept under vacuum until no further expansion of the mixture is visible. The vacuum is then stopped, and the solution is collected from the reaction vessel ready to cast. Option 2, the mixture is collected from the reaction vessel and is collected into a container and sealed, and left for several hours to degas, this is mainly possible due the unique mixture of the above ingredients, and is not typical of such emulsions. The following day the mixture is ready to be cast.

The mixture is cast by any method known to those skilled in the art of solution casting, such as the roller method described herein. As shown in FIG. 1 the film of the present disclosure may contain a matrix and the active dispersed therein. Alternatively, the insoluble active particles may be impregnated in the film matrix as shown in FIG. 2.

In one particular example, pure CBD crystal isolate powder was dissolved in solution by 30 placing flavor, polysorbate, and vegetable glycerin and heating in a temperature range of 70° F. to 250° F., or 100° F.-170° F., or about 120° F. for a period of 5-45 minutes, or 10-35 minutes or about 30 minutes to create a homogenous emulsion. After the mix was visually inspected to ensure it was sufficiently blended, the emulsion mix was pipetted into the mixing vessel that already contained water heated to 90° F.

The following substances may also be used in the preparation of the films.

Surfactant/emulsifier: Polysorbate 20 (polyoxyethylene (20) sorbitan monolaurate); Polysorbate 40 (polyoxyethylene (20) sorbitan monopalmitate); Polysorbate 15 60 (polyoxyethylene (20) sorbitan monostearate); Polysorbate 80 (polyoxyethylene (20) sorbitan monooleate); Polyethylene glycol; Monoglycerides; Diglycerides; Triglycerides; Phospholipids; Lecithin; Sodium bis(2-ethylhexyl) sulfosuccinate (AOT); or sodium mono- and dimethylnaphthalene sulfonate (SMDNS).

Carriers/softening agents: Glycerol/glycerin; Propylene Glycol; Fatty acids; 20 Vegetable oil; Vegetable shortening; Olive oil; Soybean oil; Grape seed oil; Sunflower oil; Peanut oil; Corn oil; Canola oil; Rice Bran oil; Lard; Suet; Butter or Coconut oil.

Polysaccharides and thickening agents: Acetylated distarch adipate; Agar; Alginic acid; Arrowroot; Beta-glucan; Calcium alginate; Carrageenan; Cassia Gum; Chondrin; Collagen; Corn starch; Dextrin; Disodium phosphate; Disodium pyrophosphate; 25 File powder; Galactomannan; Gelatin; Gellan Gum; Glucomannan; Guar Gum; Gulaman; Gum Karaya; Hydroxypropyl distarch phosphate; Hypromellose; *Irvingia gabonensis*; Konjac; Kudzu; Locust; Bean gum; Maltodextrin; Methyl Cellulose; Millet Jelly; Modified starch; *Monodora pyristica*; Monosodium phosphate; Mung bean; Natural Gum; Njangsa; Pullulan; Pectin; Phosphate distarch; phosphate; Polydextrose; Potassium 30 bitartrate; Potato starch; *Psyllium* seed husks; Sago; Salep; flour; Sodium phosphate; Starch; Tapioca; Tetrasodium pyrophosphate; Tragacanth; Trisodium; phosphate; Waxy corn; or Xanthan gum.

Sucralose Alternatives: Artificial Sweeteners: Acesulfame-K; Advantame; Alitame; Aspartame; Crystalline Fructose; Cyclamate; Cyclamates; Dextrose; Fruit Juice Concentrates; Glucose Syrup; High Fructose Corn Syrup; Honey; Maltodextrin; Neohesperdine; Neohesperidin DC; Neotame; Saccharin; Thaumatin; Natural Sweeteners: Brazzein; Curculin; DouxMatok Sugar; Fructose; Galactose; Glucose; 5 Glycyrrhizin; Lactose; Levulose (Fructose); Luo; Han Guo; Maltose; Miraculin; Monatin; Monellin; Monk Fruit (Luo Han Guo); Pentadin; Saccharose; *Stevia*; Stevioside; Sucrose; Sugar; Yacon Syrup; Sugars: Agave Syrup; Barley Malt; Syrup; Brown Rice Syrup; Caramel; Corn Sugar (HFCS); Corn Sweetener (HFCS); 1 Corn Syrup (HFCS); Fructose Glucose Syrup (HFCS); Glucose Fructose Syrup (HFCS); Golden Syrup; HFCS, 42; HFCS 10,55; HFCS, 90; High Fructose Corn Syrup (HFCS); High Maltose Corn Syrup (HMCS); Inverted Sugar; Isoglucose (HFCS); Modified Sugar; Refiners Syrup; Tagatose; Trehalose; Sugar Alcohols/Polyols: D-Tagatose; Erythritol; Glucitol (Sorbitol); Glycerol; HSH; HSH Hydrogenated Starch Hydroslsates; Hydrogenated Starch Hydrolysate (HSH); Isomalt (Palatinat); Lacititol; Maltitol; Mannitol; Polydextrose; Sorbitol; Xylitol; Sugar 15 Extracts: Birch Syrup; Blackstrap Molasses; Cane Juice; Coconut Palm Sugar; Fructooligosaccharide; Inulin; Isomalto, oligosaccharide (IMO); Maple Syrup; Molasses; Oligofructose; Palm Sugar; Rapadura; Sorghum Syrup; or Sugar Fiber.

Figure 5:
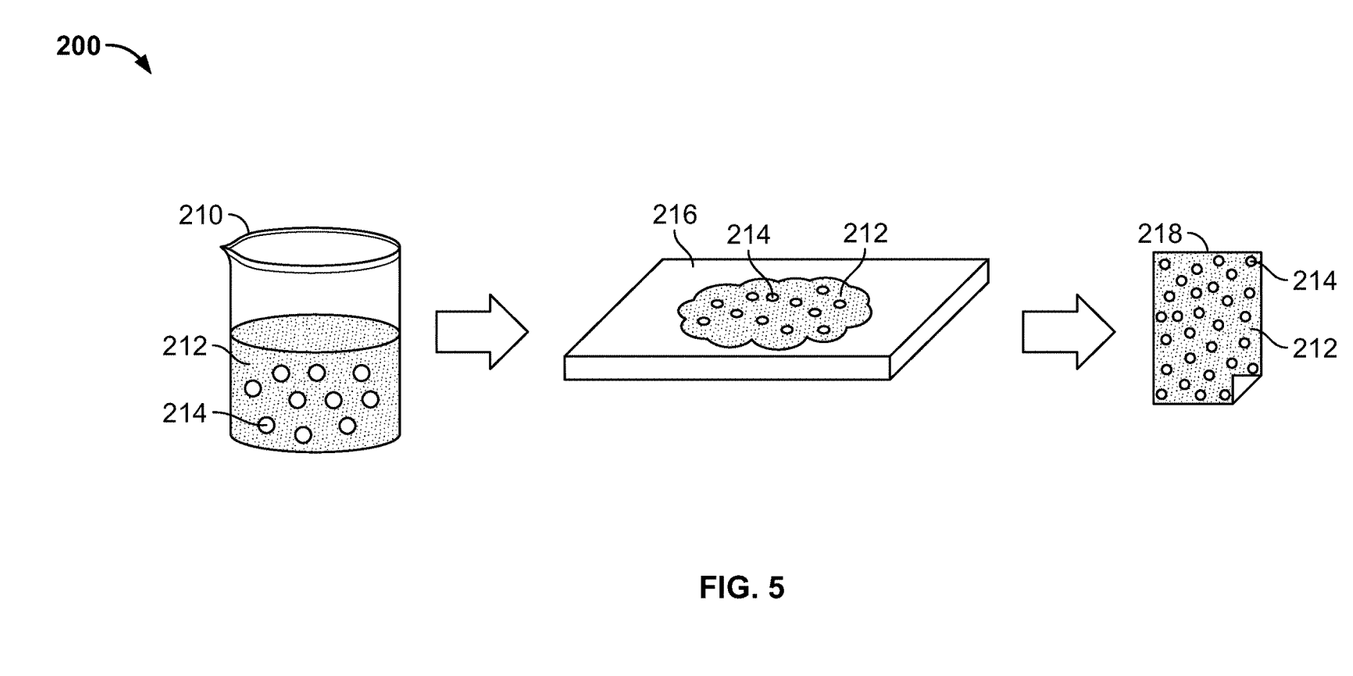
FIG. 5 is a graphic representation of a casting process for preparing a thin mucosally dissolvable film.

The preparation of the film of the present disclosure may involve any one of the following processes. As shown in FIG. 5 the process may involve a simple casting procedure. This includes a liquid composition 210 having a carrier 212 and an agent 214, which is cast into a substrate 216, and prepared into a thin film sheet 218. The casting can be into a substrate 216 that is a shaped mold or a flat plate as shown for amorphous casting. The liquid composition 210 can have ingredients that are preselected to provide a thin film sheet 218 that has one or more predetermined functionalities. The casting can include any casting steps for casting a polymeric composition into a thin film. The carrier 212 can be any type of carrier that can be cast into a thin film or other sheet as described herein. The agent 214 can be any type of chemical agent or agent particulate.

It should be noted that the same basic method depicted in FIG. 5 may be used for casting films, whether they have different drug load, different drug particle size, or if they are made from different polymers, or from different grades of a given polymer.

Figure 6:
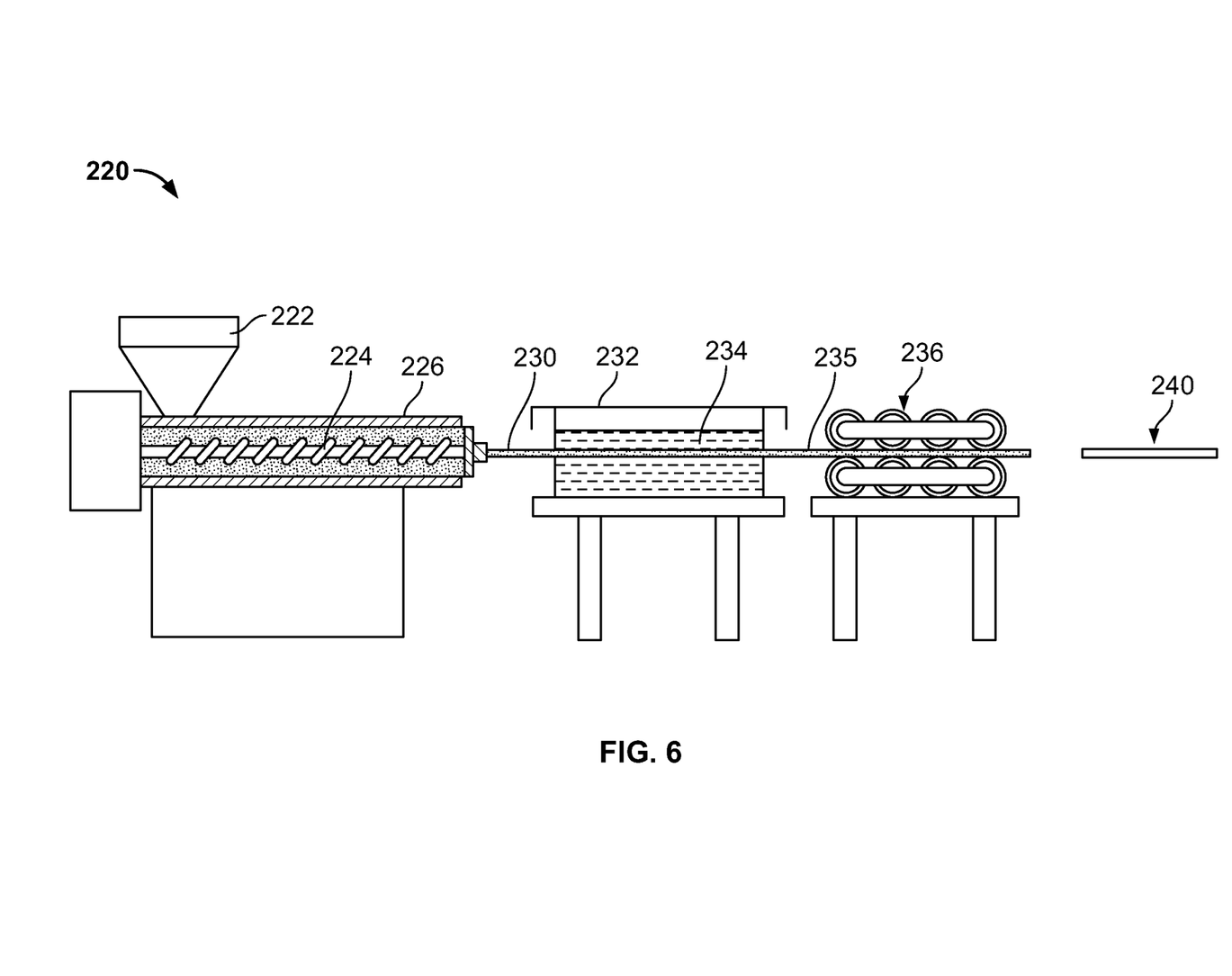
FIG. 6 is a graphic representation of an extrusion process for preparing the thin film.

The film may also be prepared by extrusion process as shown in FIG. 6. This procedure 220 can include introducing a liquid composition 210 into a hopper 222 that feeds into a screw auger mixer 224 in an extruder 226 for extruding the liquid composition 210 into an extrudate 230. The extrudate 230 may optionally be cut or pressed into a sheet of the invention. However, the extrudate 230 can be passed through a sizing plate 232 to form sized extrudate 235 that can be cut into a sheet of the invention. The extrudate 230 is shown to be cooled with a water tank 234 jacketing the sizing plate 232, so that the extrudate 230 can be cooled, if needed, while being dimensioned. The sized extrudate 235 can be processed through one or more rollers 236 so as to calender the extrudate into a thin film 237. The thin film 237 can then be cut with a cutting machine 238 into individual thin film sheets 240.

Figure 7:
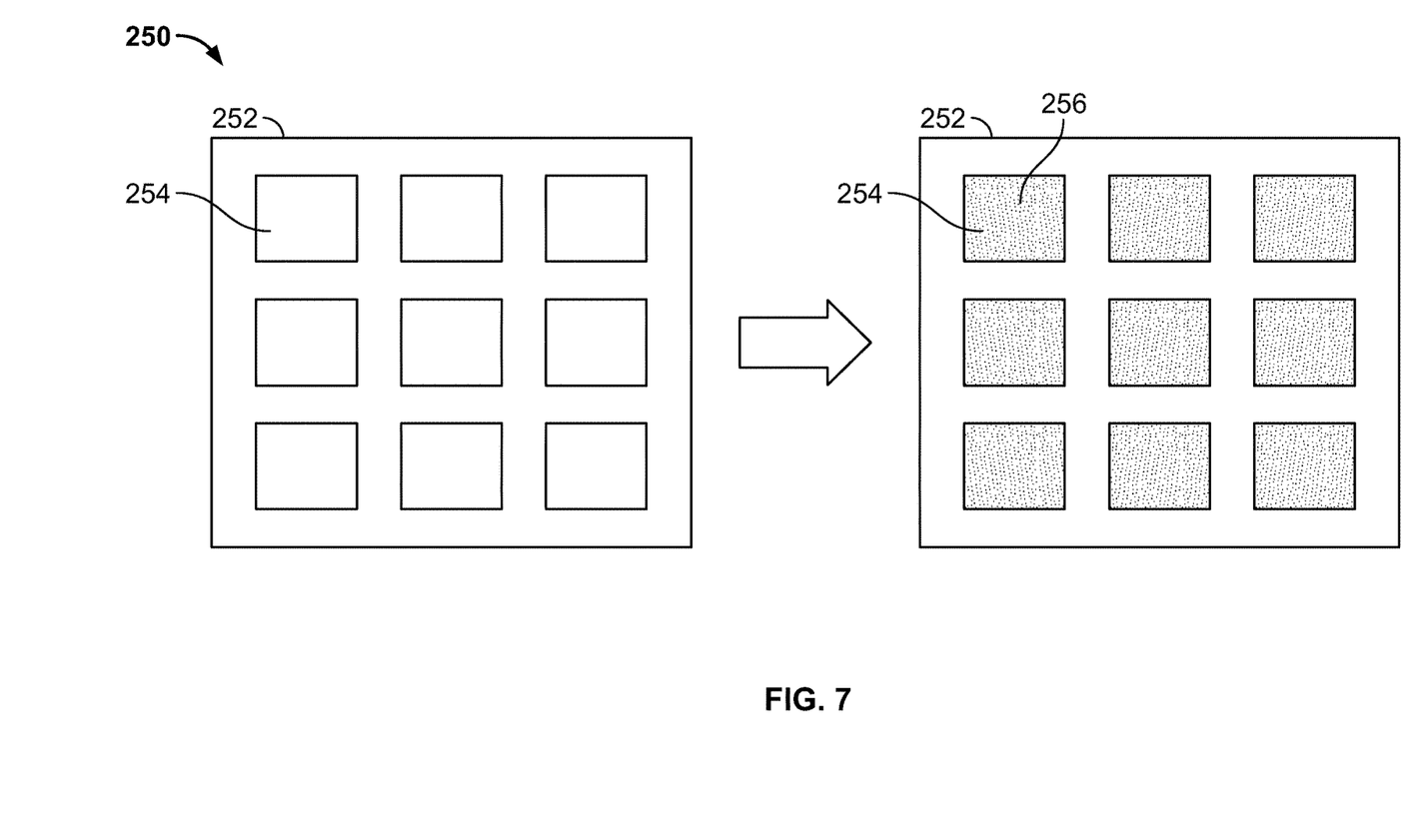
FIG. 7 is a graphic representation of a molding process for preparing the thin film.

The film of the present disclosure may also be prepared as molded thin films as shown in FIG. 7. A mold array 252 having a plurality of molds 254 can receive a liquid composition 210 in order to form the molded thin films 256 dimensioned and shaped as the mold 254. As such, each mold can be shaped to have a specific cross-sectional width and length and a specific depth in order to have a specific volume and shape. The depth can be thin as a film or thickness dimension described herein. The shape can be rectangular as shown as well as being circular, oval, triangular, square, or any other polygon or any other shape ranging from stars, hearts, or other simple shapes to complex shapes, such as animal, plant, or the like.

The film sheets can be shaped while being formed or shaped after being set. The laminates of the film sheets can also be cut into a specific shape before or after the film sheets are laminated together. The shaping can include cutting, stamping, laser-shaping, or any other method of cutting a thin film or a stack of films.

The present disclosure also provides a method of forming a self-supporting film dosage composition, including the steps of providing a carrier (e.g., polysaccharide or polymeric) matrix, providing at least one active agent, dispersing the agent throughout the matrix, and drying the matrix so as to form a self-supporting film dosage composition including agent. The agent may be in the form of a single molecule, microparticle or a nanoparticle. The film may be formed through emulsion processing, through milling, and/or through a microfluidics pumping apparatus. In some embodiments, the active may be formed via a high shear apparatus.

There is also provided a self-supporting film that includes a water soluble polymer composition including polyethylene oxide or a saccharide-based polymer. The film may also include a small scale form of the active agent. In some aspects, the film may be designed for oral administration. In other aspects, the film may be designed for mucosal (e.g., oral, vaginal, rectal) administration. As will be described in further detail below, the film is desirably substantially dissolvable when exposed to a wetting agent, such as water, alcohol or aqueous mixture of alcohols.

Each of the films prepared according to the present disclosure may be divided into smaller individual film units which may be sized and packaged to provide dosage units for consumption. The disclosure also provides a method of delivering an active agent. This method includes providing a dry film, which at least partially solubilizes when wetted, the film comprising (i) a water soluble composition; (ii) an active agent and (iii) administering the film to the user. The water soluble composition may include a saccharide-based polymer. Also provided is a self-supporting film for delivery of an active agent. This film may include a solid water soluble polymeric matrix having dispersed therein a plurality of lipophilic droplets formed from an emulsion composition having the agent. An ingestible film unit may have one discrete sheet that includes a biologically active agent.

The biologically active agent can be any agent that is administered for a function, such as a biological function to improve or otherwise modulate a biological process, such as a biological pathway. As such, the biologically active agent can be a traditional pharmaceutical or nutraceutical, and it can be any type of substance for testing or diagnostics. The biologically active agent can be any agent that is administered to a subject, human or animal, in order to elicit a biological response that arises from the biological activity of the agent. The biological response obtained can be a measurable biological response or provide some change that can be analyzed and determined, such as by testing to determine an amount of the biologically active agent to be administered. The biologically active agent can be a toxin or poison or other deleterious substance. Examples can include the biologically active agent being a mineral, vitamin, pharmaceutical, nutraceutical, small molecule, macromolecule, organic molecule, polypeptide, protein, nucleic acid, polynucleotide, derivatives thereof, and combinations thereof. The biologically active agent can be for a human or animal subject. Human and veterinary medicines can be improved with the present invention. Alternatively, each discrete sheet can be devoid of a biologically active agent when the ingestible unit is a placebo. Substances from hemp or *cannabis*, such as CBD or THC may be examples.

The films may be prepared from any type of film or laminate forming material. That is, any material that can be formed into a thin film can be used as a sheet having a particular function of the present invention. The film-forming material can range from polymers that are natural or synthetic. However, the film-forming material may be a substance other than a polymer. In one example, the film-forming material can be calcium phosphate, talc, calcium silicate, calcium carbonate, derivatives thereof, and combinations thereof, where calcium embodiments may be formed into laminates. In one example, the film-forming material can be a carrageenan.

The films may also be formed from an inorganic component. The inorganic component can be prepared into a laminate sheet. Some non-limiting examples of inorganic components that can be prepared into the discrete sheets include calcium phosphate, calcium silicate, calcium carbonate, derivatives thereof, and combinations thereof. Some inorganic materials can be formed into ceramic thin films or laminates.

The film units of the present disclosure may include at least one water soluble polymer. The films may also include water swellable or water insoluble polymers, if desired.

The self-supporting film may also include a saccharide-based polymer, which is water soluble. For example, the saccharide-based polymer may be cellulose or a cellulose derivative. Specific examples of useful saccharide-based, water soluble polymers include, but are not limited to, polydextrose, pullulan, hydroxypropylmethyl cellulose (HPMC), hydroxyethyl cellulose (HPC), hydroxypropyl cellulose, carboxymethyl cellulose, sodium aginate, xanthan gum, traganeanth gum, guar gum, acacia gum, arabic gum, starch, gelatin, and combinations thereof.

The saccharide-based polymer may be at least one cellulosic polymer, polydextrose, or combinations thereof. The film may also include non-saccharide-based, water soluble or water insoluble polymers. Examples of non-saccharide based, water soluble polymers include polyethylene oxide, polyvinylpyrrolidone, polyvinyl alcohol, polyethylene glycol, polyacrylic acid, methylmethacrylate copolymer, carboxyvinyl copolymers, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

The polymer may also be a combination of substances, such as hydroxypropylmethyl cellulose and polyethylene oxide; polydextrose and polyethylene oxide or polydextrose, hydroxy propylmethyl cellulose and polyethylene oxide.

As used herein, the phrase "water soluble polymer" and variants thereof refer to a polymer that is at least partially soluble in water, and desirably fully or predominantly soluble in water, or absorbs water.

The film unit of the present disclosure is at least partially dissolvable when exposed to a wetting agent or may be substantially dissolvable when exposed to a wetting agent. The film of the present disclosure may be absorbed through the mucosal tissue within about 20 seconds, or about 30 seconds, or about 40 seconds or about 60 seconds. Unlike prior art films which dissolves very quickly or instantaneously in the mouth allowing the active agents to break down in the digestive tract, the film of the present disclosure dissolves slowly so that the bulk of the active agent seeps through the mucosal tissue of the subject.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present disclosure include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of a-benzyl glutamate and polyethylene glycol, copolymers of succinate and poly(glycols), polyphosphazene, polyhydroxy-alkanoates and mixtures thereof. Binary and ternary systems are contemplated.

Other specific polymers that may be suitable include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (225°–235° C.); lactide/glycoli 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point 30 within the range of 338°–347° F. (170°–175° C.).

Although a variety of different polymers may be used, it is desired to select polymers to provide a desired viscosity of the mixture prior to drying. For example, if the topical agent or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability in an emulsion, a colloid or a suspension. Generally, the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process. The viscosity may be adjusted based on the selected agent component, depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

When the active agent is a biologically active agent or anti-counterfeiting agent, then it may be included as particles in the discrete sheets. The particles can be embedded entirely within the sheet matrix or embedded in a surface to provide a rough profile. Some particles may be exposed in the surface. The particles can be obtained or prepared by aggregating a number of agent molecules together. The size of the particles can vary or be uniform. Preferred particle sizes can range from about 10 nm to about 1000 microns, from about 1 micron to about 50 microns, and from about 10 microns to about 100 microns. Also, the sheets having the particles can be prepared on-site or obtained from a supplier. The sheets can be made by: preparing a plurality of particles having a biologically active agent; suspending the plurality of particles in a composition; and forming the composition into a discrete sheet. The sheets can include a high load of particles, which can be about 50% by weight or +/−10% or 20%. This can allow for the ingestible unit to include as much drug as current tablets or capsules, which can be over 1000 mg in some instances, but usually containing low hundreds of milligrams. The sheets can include a low load of particles, which can be about 5% to 1% by weight. The sheets can include a very low of particles, which can be about 1% or less.

The biologically active agent can also be a nutritional supplement, such as iron, which is difficult to administer with proper absorption. Iron is soluble in acidic pH, and usually precipitates in the intestine at neutral pH. Now, one or more pH-modifying sheets that produce an acidic environment or microenvironment can be included with the iron sheet. Similarly, other specific functionalities can be provided to improve the absorption of biologically active agents. Also, complexing and/or chelating agents can be included in sheets to complex with agents to facilitate absorption from the intestine.

Treatment of Disorders

The disintegration of the film can occur within about 60 seconds upon coming in contact with water, such as the saliva, stomach fluid, or delayed to occur in the small or large intestines. The disintegration may also occur immediately upon coming in contact with saliva, producing a predefined breakage pattern into smaller pieces for easier mucosal delivery.

The film strips described herein having the CBD and/or THC can be used for treatments known in the art. CBD could be used for treating symptoms of rheumatoid arthritis and other autoimmune diseases, diabetes, nausea, bowel disorders, inflammation, provide neuroprotective effects, and provide anti-cancer effects, and reduce many other hard-to-control side effects of other medications. THC can be used to treat aches, pains, backache, muscle stiffness, joint pain, inflammation, and reduce many other hard-to-control side effects of other medications or anticancer treatments. The THC can be used to provide anti-emetic, appetite enhancing, relaxation, analgesia, and therapeutic use in Tourette's syndrome, treat dystonia and tardive dyskinesia, treat nausea, treat vomiting, treat anorexia, treat cachexia, treat spasticity, treat movement disorders, treat Multiple Sclerosis, treat pain (rheumatoid arthritis, cancer pain, headache, menstrual pain, chronic bowel inflammation and neuralgias), treat glaucoma, treat epilepsy, treat asthma, treat addiction, treat substance dependency, treat withdrawal symptoms, treat psychiatric symptoms, treat autoimmune diseases, treat inflammation (e.g. ulcerative colitis, arthritis), 10 and many others, and may be used to treat pruritis, hiccup, attention deficit syndrome, high blood pressure, tinnitus, chronic fatigue syndrome, restless leg syndrome, insomnia, depression, anxiety, stress, situational sadness (e.g., from death in family), and any others.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. A film consisting essentially of:
an emulsion of an extract of *cannabis*;
pullulan;
hydroxypropylmethyl cellulose acetate succinate;
polysorbate;
pectin;
guar gum;
coconut oil; and
sucralose, wherein the film is mucosally dissolvable.

2. The film of claim 1, wherein the extract of *cannabis* consists essentially of cannabinoids and/or tetrahydrocannabinol.

3. The film of claim 1, wherein the extract of *cannabis* is in a concentration greater than about 90%.

4. The film of claim 1, wherein the extract of *cannabis* is in a range from about 1% to about 70% by weight of the film.

5. The film of claim 1, wherein the sucralose is present in an amount of about 0.001% to about 0.5% by weight of the film.

6. A film consisting essentially of:
an emulsion of an extract of *cannabis*;
pullulan;
hydroxypropylmethyl cellulose acetate succinate;
polysorbate;
pectin;
guar gum;
coconut oil;
niacin; and
sucralose, honey, or *stevia*, wherein the film is mucosally dissolvable.

7. The film of claim 6, wherein the extract of *cannabis* consists essentially of cannabinoids and/or tetrahydrocannabinol.

8. The film of claim 6, wherein the extract of *cannabis* is in a concentration greater than about 90%.

9. The film of claim 6, wherein the extract of *cannabis* is in a range from about 1% to about 70% by weight of the film.

10. The film of claim 6, wherein the sucralose, honey, or *stevia* is present in an amount of about 0.001% to about 0.5% by weight of the film.

11. The film of claim 6, wherein the niacin is present in an amount of about 0.001% to about 10% by weight of the film.

12. A film consisting essentially of:
an emulsion of an extract of *cannabis*;
pullulan;
hydroxypropylmethyl cellulose acetate succinate;
polysorbate;
pectin;
guar gum;
coconut oil;
menthol; and
sucralose, honey, or stevia, wherein the film is mucosally dissolvable.

13. The film of claim 12, wherein the extract of *cannabis* consists essentially of cannabinoids and/or tetrahydrocannabinol.

14. The film of claim 12, wherein the extract of *cannabis* is in a concentration greater than about 90%.

15. The film of claim 12, wherein the extract of *cannabis* is in a range from about 1% to about 70% by weight of the film.

16. The film of claim 12, wherein the sucralose, honey, or *stevia* is present in an amount of about 0.001% to about 0.5% by weight of the film.

17. The film of claim 12, wherein the menthol is present in an amount of about 0.001% to about 10% by weight of the film.

18. A film consisting essentially of an emulsion of an extract of *cannabis*, pullulan and hydroxypropylmethyl cellulose acetate succinate, and wherein the film is mucosally dissolvable.

* * * * *